(12) United States Patent
Hunt

(10) Patent No.: US 7,304,305 B2
(45) Date of Patent: Dec. 4, 2007

(54) DIFFERENCE-FREQUENCY SURFACE SPECTROSCOPY

(75) Inventor: Jeffrey H. Hunt, Chatsworth, CA (US)

(73) Assignee: The Boeing Company, Chicago, IL (US)

( * ) Notice: Subject to any disclaimer, the term of this patent is extended or adjusted under 35 U.S.C. 154(b) by 797 days.

(21) Appl. No.: 10/174,640

(22) Filed: Jun. 19, 2002

(65) Prior Publication Data

US 2003/0234360 A1    Dec. 25, 2003

(51) Int. Cl.
*G01N 21/35* (2006.01)
(52) U.S. Cl. .................. 250/339.06; 356/300
(58) Field of Classification Search ........... 250/339.06; 356/300
See application file for complete search history.

(56) References Cited

U.S. PATENT DOCUMENTS

| | | | |
|---|---|---|---|
| 4,215,274 A * | 7/1980 | Segall | 250/361 R |
| 4,639,923 A * | 1/1987 | Tang et al. | 372/21 |
| 5,294,289 A | 3/1994 | Heinz et al. | |
| 5,623,341 A | 4/1997 | Hunt | |
| 5,658,148 A * | 8/1997 | Neuberger et al. | 433/215 |
| 5,875,029 A | 2/1999 | Jann et al. | |
| 5,883,714 A | 3/1999 | Jann et al. | |
| 5,898,499 A | 4/1999 | Pressesky | |
| 5,923,423 A | 7/1999 | Sawatari et al. | |
| 5,973,778 A | 10/1999 | Hunt | |
| 6,317,514 B1 | 11/2001 | Reinhorn et al. | |
| 6,359,451 B1 | 3/2002 | Wallmark | |
| 2003/0152691 A1 * | 8/2003 | Baude et al. | 427/96 |

OTHER PUBLICATIONS

"Light Waves at the Boundary of Nonlinear Media"—The Physical Review, 128, p. 193, 1962, Bloembergen and P.S. Pershan.
"Surface Studies by Optical Second Harmonic Generation: an Overview"—Journal of Vacuum Science and Technology B, vol. 3, No. 5, Sep. Oct. 1985, pp. 1464-1466, Y.R. Shen.

* cited by examiner

*Primary Examiner*—David Porta
*Assistant Examiner*—Shun Lee
(74) *Attorney, Agent, or Firm*—Ingrassia Fisher Lorenz, P.C.

(57) ABSTRACT

A fixed visible input and tunable visible input are directed to a location on a surface to be interrogated. The fixed visible input and the tunable visible inputs are aligned so that their surface locations of optical illumination overlap on the interrogated location. An output wavelength discriminator receives the reflected difference-frequency generated on the interrogated location. The output wavelength discriminator is substantially non-transmissive at frequencies higher than the difference-frequency, but substantially transmissive at the difference-frequency of the fixed visible input and the tunable visible input. Signal collection optics receives an output of the output wavelength discriminator and directs the propagation of the output thereof so that a collected optical light signal is formed after propagation through the signal collection optics. The collected optical light signal is converted to an electronic signal. Thus, the intensity of the difference-frequency wavelength is monitored for providing surface-sensitive infrared spectroscopic characterizations on the surface to be interrogated.

20 Claims, 1 Drawing Sheet

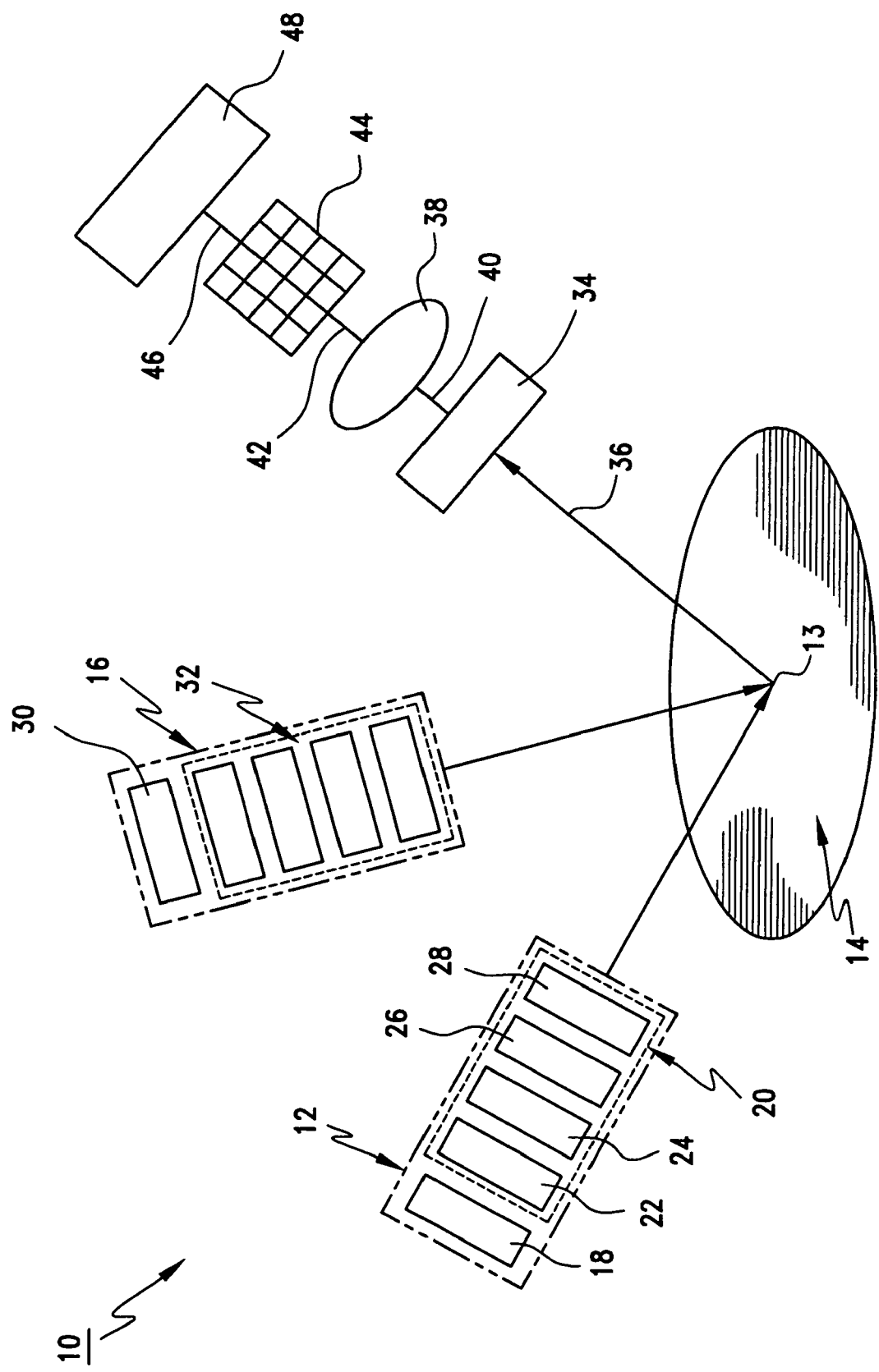

DIFFERENCE-FREQUENCY SURFACE SPECTROSCOPY

BACKGROUND OF THE INVENTION

1. Field of the Invention

The present invention relates to monitoring contamination on a surface and more particularly to the use of second-order nonlinear optics to determine the level of contamination with a high degree of specificity.

2. Description of the Related Art

In nonlinear optical, or so-called wave mixing processes, outputs are produced at sum, difference or harmonic frequencies of the input(s). Second order nonlinear optics or three-wave mixing involves combining two inputs to produce one output at one of these combination frequencies. Using second order nonlinear optical surface spectroscopy to examine the physical properties and behavior of a surface or interface was originally proposed in the 1960's, in "Light Waves at the Boundary of Nonlinear Media" by Bloembergen and P. S. Pershan, The Physical Review, 128, Page 193 (1962). Experimental work involving second harmonic generation was also performed. The authors of the publication realized that, under certain conditions, second order nonlinear optical effects would be constrained to a surface. However, because lasers at the time were comparatively feeble, impractical, slow, etc., there was little subsequent work done on the development of second harmonic generation or, more generally, second order nonlinear optical (NLO) processes at surfaces until considerably later, when lasers had reached a certain level of technical maturity.

Recently, researchers have reviewed NLO processing and concluded that lasers had developed enough that they could be used for studying the physical and chemical properties of surfaces and interfaces. For example, a theoretical study of the physics of the interface, and not its engineering aspects, has been performed. See Journal of Vacuum Science and Technology B, Volume 3, Number 5, September October 1985, Pages 1464-1466, Y. R. Shen, "Surface Studies by Optical Second Harmonic Generation: an Overview." The physical properties which make second order nonlinear optics useful for surface sensitive characterizations are discussed in this publication.

In U.S. Pat. No. 5,294,289, T. F. Heinz et al. discuss the use of second harmonic generation as a means to monitor the epitaxial growth of silicon semiconductor structures in a high vacuum chamber. Specifically, they examined the spectroscopic response at the interface between the electronically active silicon and the insulative layer of calcium fluoride. Changing the wavelength of the input induced a resonant enhancement of the intensity of the surface second harmonic signal. By monitoring the magnitude of the resonance, they could ascertain whether the insulator was present on the surface and whether it had electronically binded to the underlying semiconductor. The system that is used examines the total intensity only of the second harmonic light that is generated and there is no discussion of the use of optical difference-frequency generation between two input sources. There is also no discussion of contamination detection.

In U.S. Pat. No. 5,623,341, J. H. Hunt discusses the use of sum-frequency generation for the detection of contamination and corrosion on engine parts. In this incarnation, one of the inputs is a tunable IR beam that is tuned to a resonance of the contamination or corrosion on the surface. The efficiency of the sum-frequency process is increased (so-called resonant enhancement) when the IR beam is resonant with a contaminant. If the contaminant is not present, there is no resonant enhancement. By comparing on and off resonant signals, the presence and level of contaminant can be deduced. However, there is no discussion of applying difference-frequency generation to observe a material resonance.

In U.S. Pat. No. 5,875,029, P. C. Jann et al. describe a versatile optical inspection instrument and method to inspect magnetic disk surfaces for surface defects. The device provides surface position information of the defects. However, the technique involves only linear optical processes. That is, the input and output light wavelengths are the same. There is also no discussion of contamination.

In U.S. Pat. No. 5,883,714, Jann et al. describe a versatile optical inspection instrument and method to inspect magnetic disk surfaces for surface defects. The device is based on interferometric measurement and detects contaminants by measuring the Doppler shift in the light that results from scanning the light onto a contaminant or defect. By scanning, the device provides surface position information of the defects. However, the technique involves only linear optical processes and senses only phase changes. That is, the input and output light wavelengths are the same and there is no discussion of contamination.

In U.S. Pat. No. 5,898,499, J. L. Pressesky discusses a system for detecting local surface discontinuities in magnetic storage discs. The device is an interferometric detector which scans the disc in a spiral motion. Local defects cause local changes in phase which are measured by interferometric techniques. This is a linear optical technique.

In U.S. Pat. No. 5,932,423, T. Sawatari et al. discuss a scatterometer for detecting surface defects in semiconductor wafers. This device is a linear interferometric device.

In U.S. Pat. No. 5,973,778, J. H. Hunt discusses the use of second harmonic generation for investigating molecular alignment within a thin polyimide film. The technique uses changes in the second harmonic polarization to determine surface molecular alignment. There is no discussion of difference-frequency generation from the surface to be interrogated. Furthermore, there is no discussion of semiconductor materials or contamination. The nonlinear optical response of a semiconductor will be quite different than that of a liquid crystal film.

In U.S. Pat. No. 6,317,514 B1, S. Reinhorn et al. discuss a method and apparatus for inspecting a wafer surface to detect the presence of conductive material on the wafer. The device uses UV initiated electron emission to determine the location of conductive areas. Those areas which are metal will emit electrons. If the area, which is supposed to be conductive, is not, there will be no electron emission.

In U.S. Pat. No. 6,359,451 B1, G. N. Wallmark discusses a system for testing for opens and shorts between conductor traces on a circuit board. The technique uses electron scattering to perform its diagnostics and has no optics associated with it.

SUMMARY

The present invention is a nonlinear optical system for performing surface-sensitive infrared spectroscopic characterizations on a surface to be interrogated. In a broad aspect, the present invention includes a first optical source for providing a fixed visible input directable to a location on a surface to be interrogated. A second optical source provides a tunable visible input that is directable to the surface to be interrogated. The fixed visible input and the tunable visible inputs are alignable so that their surface locations of optical illumination overlap on the interrogated location. An output wavelength discriminator receives the reflected difference-frequency generated on the interrogated location. The output wavelength discriminator is substantially non-transmissive at frequencies higher than the difference-frequency, but substantially transmissive at the difference-frequency of the fixed visible input and the tunable visible input. The output of the output wavelength discriminator is infrared. Signal collection optics receives an output of the output wavelength discriminator and directs the propagation of the output of the output wavelength discriminator so that a collected optical light signal is formed after propagation through the signal collection optics. An optical detector converts the collected optical light signal to an electronic signal. Thus, the intensity of the difference-frequency wavelength is monitored for providing surface-sensitive infrared spectroscopic characterizations on the surface to be interrogated.

Ordinarily, the characterization of the spectroscopic properties of a material requires an optical source at the desired range of wavelengths. Infrared spectroscopy requires an optical source which generates light in the infrared. However, when studying the nonlinear optical response of a material, resonant behavior can be achieved even if only the difference between two input sources corresponds to a material resonance. In many cases, it is difficult to generate infrared light at arbitrary wavelengths, but it is always possible to generate tunable visible light, whose wavelength can be tuned near the wavelength of a fixed visible source. In the present case, where nonlinear optical processes are being used to monitor a surface, it is important that the input sources have high peak power. It is difficult to produce high peak power optical pulses at arbitrary infrared wavelengths. Instead, difference-frequency allows the use of visible high peak power pulses, which are easier to produce, to make the same measurements.

Other objects, advantages, and novel features will become apparent from the following detailed description of the invention when considered in conjunction with the accompanying drawings.

BRIEF DESCRIPTION OF THE DRAWING

FIG. 1 is a schematic representation of the nonlinear optical system of the present invention.

DETAILED DESCRIPTION OF THE INVENTION

Referring now to the drawings and the characters of reference marked thereon, FIG. 1 illustrates a preferred embodiment of the nonlinear optical system of the present invention, designated generally as 10. Diagnostic system 10 includes a first optical source, indicated by phantom lines 12 for providing a fixed visible input that is directable to a location 13 on a surface 14 of the semiconductor wafer to be interrogated. A second optical source 16 provides a tunable visible input that is also directable to the location 13 on the surface 14 to be interrogated. The optical sources 12, 16 are aligned so that their surface areas of optical illumination overlap on the interrogated surface 14. This alignment may be implemented via a series of refractive and reflective elements. For example, by changing their tilt in two axes, two mirrors in series can propagate a laser beam to any position on a surface.

The first optical source 12 includes a fixed visible input 18 in optical communication with an associated input optics 20. The input 18 is preferably a narrow frequency bandwidth visible pulse laser and, may be, for example a pulsed diode laser, a continuous wave diode laser or a pulsed solid state laser or a continuous wave solid state laser.

The input optics 20 preferably includes an input polarizer 22, an input wavelength discriminator 24, an input spatial filter 26 and an input propagation optics 28. The input polarizer 22 could be, for example, a brewster angle polarizer, a thin film polarizer, a Glan-air or Glan-Thompson polarizer or other crystal polarizer. The wavelength discriminator 24 may be, for example, a color filter, a dielectric film, a holographic transmission filter or a grating. The input propagation optics 20 could be formed of one or more refractive or reflective optics which, when used in combination, control the divergence or convergence of the beam as it propagates towards the surface.

The second optical source 16 includes a tunable visible input 30 and associated input optics 32. The input optics 32 may be as described above with respect to the first optical source 12. However, the optics 32 is optimized for the wavelength of the second optical source 16. The input 30 is preferably a tunable visible laser and may be, for example, an optical parametric oscillator whose optical resonator may be designed so that the output light will be tunable at wavelengths in the vicinity of the fixed wavelength. The tunable visible source pulse should cover substantially the entire visible range required so that the difference-frequency with the fixed source will cover the infrared response of contamination that may be present on the surface 14.

An output wavelength discriminator 34 receives the reflected difference-frequency 36 generated on the interrogated location 13. The output wavelength discriminator 34 is substantially non-transmissive at frequencies higher than the difference-frequency, but is substantially transmissive at the difference-frequency of the fixed visible input 18 and the tunable visible input 30. The output 40 of the output wavelength discriminator is an infrared output. The output wavelength discriminator 34, like the input wavelength discriminator, may comprise a color filter, a dielectric film, a holographic transmission filter or a grating. The output wavelength discriminator is necessary to assure that only reflected light at the difference-frequency, and no light at the input visible wavelengths, are monitored.

Signal collection optics 38 receives the infrared output 40 of the output wavelength discriminator 34 and directs the propagation of the output so that a collected optical light signal 42 is formed after propagation through the signal collection optics 38. The signal collection optics 38 may be either refractive or reflective optics which, when used in conjunction, act to control the divergence of the light coming from the surface so that as much of the light signal, as is technically possible, is collected for subsequent analysis.

An optical detector 44 converts the collected optical light signal 42 to an electronic signal 46, thus monitoring the intensity of the difference-frequency wavelength as a function of semiconductor wafer contamination. The optical detector 44 may be, for example, an avalanche photodiode, which creates an electronic signal proportional to the amount of light incident on it.

An electronic signal analyzer 48 analyzes the electronic signal 46 for providing surface-sensitive infrared spectroscopic characterizations. The electronic signal analyzer 48 may be, for example, a computer with suitable internal electronics to implement the appropriate mathematical algorithms to interpret the signals.

The presence of contamination on the surface will change the spectroscopic response of the surface. Since the amount of light generated at the difference-frequency wavelength will depend upon the surface spectroscopy, appropriate interpretation of the electronic signal provides a means to monitor the amount of contamination present on the surface.

In a preferred embodiment the first optical source may comprise a Nd:YAG laser operating on the 1.064 micron line or a Nd:YAG laser and a harmonic converter for operation at the second or third harmonic of the laser fundamental output wavelength. It may operate with a maximum pulse length of 10 nanoseconds. The optimal pulse length is less than 1 picosecond.

The input optics of the first optical source preferably includes a steering apparatus, comprising two mirrors aligned so that that their surface normals are non-coplanar. It also preferably includes a polarization rotator comprising a half-wave plate. The half-wave plate should be optimized for an output wavelength of the input laser. The input optics also preferably uses a linear polarizer that is aligned so that an output wavelength is p or s polarized with the polarization referenced to the surface to be interrogated. A spot shaping apparatus is used, comprising a series of lenses, for creating a controlled spot size on the surface to be interrogated. Finally, a narrow band optical filter is used that passes only an output wavelength or harmonic wavelength of the input laser.

In this preferred embodiment, the second optical source preferably comprises a tunable visible input—an optical parametric oscillator and amplifier tunable output in a band of 0.2 to 1.0 micron. A steering apparatus is utilized including two mirrors aligned so that that their surface normals are non-coplanar, with the mirrors' reflectances being optimized for an output wavelength of the tunable visible laser. A polarization rotator is used that is operative in the visible range. A linear polarizer is used and is aligned so that an output wavelength is p or s polarized with the polarization referenced to the surface to be interrogated. Again, a spot shaping apparatus is used, including a series of lenses for creating a controlled spot size on the surface to be interrogated, the lenses being transparent in the visible range. Finally, an optical filter is utilized including a color filter having a bandgap that passes visible, but blocks longer, wavelengths.

The output wavelength discriminator preferably includes an iris; a filter in optical communication with the iris for passing the difference-frequency wavelength; and, a linear polarizer in optical communication with the filter, aligned to detect either the p or s polarized difference-frequency wavelength, wherein the polarization is referenced to the surface where the difference-frequency light is generated.

The signal collection optics preferably includes a telescope system comprising a plurality of telescope system lenses having materials and coatings optimized for the difference-frequency wavelength, which will be in the infrared, in the wavelength band from 2.0 to 10.0 micron. The optical detector may be based on one of several semiconductors, such as silicon, germanium, etc, depending on the exact infrared wavelength to be detected. The detector will be electronically gated to only detect output light generated by the input laser pulses. A computer collects and analyzes the electronic data from the optical detector.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

The invention claimed is:

1. A nonlinear optical system for performing surface-sensitive infrared spectroscopic characterizations on a surface to be interrogated, comprising:

a) a first optical source for providing a fixed visible input directable to a location on a surface to be interrogated, wherein said fixed visible input is provided at a first visible frequency;

b) a second optical source for providing a tunable visible input being directable to said surface to be interrogated, wherein:

said tunable visible input is provided at a second visible frequency that is tunable so that the difference-frequency between said first visible frequency and said second visible frequency is at an infrared frequency; and said fixed visible input and said tunable visible input are alignable so that their surface locations of optical illumination overlap on said interrogated location generating said difference-frequency from said surface overlap location;

c) an output wavelength discriminator for receiving said reflected infrared difference-frequency generated on said interrogated location, said output wavelength discriminator being substantially non-transmissive at frequencies higher than said difference-frequency, but being substantially transmissive at said difference-frequency of said fixed visible input and said tunable visible input, the output of said output wavelength discriminator being an infrared output;

d) signal collection optics for receiving said output of said output wavelength discriminator and directing the propagation of said output of the output wavelength discriminator so that a collected optical light signal is formed after propagation through said signal collection optics; and e) an optical detector for converting said collected optical light signal to an electronic signal, thus monitoring the intensity of said infrared difference-frequency as a function of the interrogated surface contamination and observing a material resonance for providing surface-sensitive infrared spectroscopic characterizations on the surface to be interrogated.

2. The nonlinear optical system of claim 1, further comprising an electronic signal analyzer for analyzing said electronic signal for providing the surface-sensitive infrared spectroscopic characterizations.

3. The nonlinear optical system of claim 1, wherein said first optical source comprises a first laser in optical communication with a first input optics.

4. The nonlinear optical system of claim 1, wherein said first optical source comprises a first laser in optical communication with a first input optics, said first input optics comprising a first input polarizer, a first input wavelength discriminator, a first input spatial filter and first input propagation optics in optical communication.

5. The nonlinear optical system of claim 1, wherein said second optical source comprises a second laser in optical communication with a second input optics.

6. The nonlinear optical system of claim 1, wherein said second optical source comprises a second laser in optical communication with a second input optics, said second input optics comprising a second input polarizer, a second input wavelength discriminator, a second input spatial filter and second input propagation optics in optical communication.

7. The nonlinear optical system of claim 1, wherein said second optical source comprises an optical parametric oscillator and amplifier tunable output in a band of 0.2 to 1.0 micron.

8. The nonlinear optical system of claim 1, wherein said first optical source comprises a pulsed solid state laser.

9. The nonlinear optical system of claim 1, wherein said optical detector comprises an avalanche photodiode.

10. A nonlinear optical system for performing surface-sensitive infrared spectroscopic characterizations on a surface to be interrogated, comprising:
   a) a visible pulse laser for providing a fixed visible input directable to a location on a surface to be interrogated, wherein said fixed visible input is provided at a first visible frequency, and wherein said fixed visible input is in optical communication with a first input optics;
   b) a tunable visible laser for providing a tunable visible input being directable to said surface to be interrogated, wherein:
      said tunable visible input is in optical communication with a second input optics;
      said tunable visible input is provided at a second visible frequency that is tunable;
      so that the difference-frequency between said first visible frequency and said second visible frequency is at an infrared frequency; and
      said fixed visible input and said tunable visible input are alignable so that their surface locations of optical illumination overlap on said interrogated location generating said difference-frequency from said surface overlap location;
   c) an output wavelength discriminator for receiving said reflected infrared difference-frequency generated on said interrogated location, said output wavelength discriminator being substantially non-transmissive at frequencies higher than said difference-frequency, but being substantially transmissive at said difference-frequency of said fixed visible input and said tunable visible input, the output of said output wavelength discriminator being an infrared output;
   d) signal collection optics for receiving an output of said output wavelength discriminator and directing the propagation of said output of the output wavelength discriminator so that a collected optical light signal is formed after propagation through said signal collection optics;
   e) an optical detector for converting said collected optical light signal to an electronic signal, thus monitoring the intensity of said infrared difference-frequency as a function of material resonance at infrared wavelengths on the surface to be interrogated and observing said material resonance for providing surface-sensitive infrared spectroscopic characterizations on the surface to be interrogated; and
   f) an electronic signal analyzer for analyzing said electronic signal to observe material resonances as a function of said infrared difference-frequency for providing the surface-sensitive infrared spectroscopic characterizations using visible inputs.

11. The nonlinear optical system of claim 10, wherein said second optical source comprises an optical parametric oscillator and amplifier tunable output in a band of 0.2 to 1.0 micron.

12. The nonlinear optical system of claim 10, wherein said first optical source comprises a pulsed solid state laser.

13. The nonlinear optical system of claim 10, wherein said optical detector comprises an avalanche photodiode.

14. A method for performing surface-sensitive infrared spectroscopic characterizations on a surface to be interrogated, comprising:
   a) directing a fixed visible input provided at a first visible frequency to a location on a surface to be interrogated;
   b) directing a tunable visible input provided at a second tunable frequency to said surface to be interrogated such that the difference-frequency between said first visible frequency and said second visible frequency is at an infrared frequency, said fixed visible input and said tunable visible input being alignable so that their surface locations of optical illumination overlap on said interrogated location generating said difference-frequency from said surface overlap location;
   c) receiving the reflected infrared difference-frequency generated on said interrogated location, via an output wavelength discriminator, said output wavelength discriminator being substantially non-transmissive at frequencies higher than said difference-frequency, but being substantially transmissive at said difference-frequency of said fixed visible input and said tunable visible input, the output of said output wavelength discriminator being an infrared output;
   d) receiving an output of said output wavelength discriminator, via a signal collection optics, and directing the propagation of said output of the output wavelength discriminator so that a collected optical light signal is formed after propagation through said signal collection optics; and
   e) converting said collected optical light signal to an electronic signal, thus monitoring the intensity of said infrared difference-frequency as a function of material resonance at infrared wavelengths on the surface to be interrogated for providing surface-sensitive infrared spectroscopic characterizations using visible inputs on the surface to be interrogated.

15. The method of claim 14, further comprising the step of analyzing said electronic signal for providing the surface-sensitive infrared spectroscopic characterizations.

16. The method of claim 14, wherein said step of directing a fixed visible input comprises directing a pulsed diode laser.

17. The method of claim 14, wherein said step of directing a fixed visible input comprises directing a continuous wave diode laser.

18. The method of claim 14, wherein said step of directing a fixed visible input comprises directing a pulsed solid state laser.

19. The method of claim 14, wherein said step of directing a fixed visible input comprises directing a continuous wave solid state laser.

20. The method of claim 14, wherein said step of directing a tunable visible input comprises directing an optical parametric oscillator.

* * * * *